US012589001B2

(12) United States Patent
Jiang et al.

(10) Patent No.: US 12,589,001 B2
(45) Date of Patent: Mar. 31, 2026

(54) THREE-DIMENSIONAL PRINTED BONE DEFECT REPAIR SCAFFOLD AND PREPARATION METHOD THEREOF

(71) Applicant: Affiliated Stomatology Hospital of Guangzhou Medical University, Guangzhou (CN)

(72) Inventors: Qianzhou Jiang, Guangzhou (CN); Xinran Tu, Guangzhou (CN); Lvhua Guo, Guangzhou (CN); Guozhong Tan, Guangzhou (CN); Rongfeng Chen, Guangzhou (CN); Yang Zhang, Guangzhou (CN)

(73) Assignee: Affiliated Stromatology Hospital of Guangzhou Medical University, Guangzhou (CN)

( * ) Notice: Subject to any disclaimer, the term of this patent is extended or adjusted under 35 U.S.C. 154(b) by 639 days.

(21) Appl. No.: 18/124,602

(22) Filed: Mar. 22, 2023

(65) Prior Publication Data

US 2023/0301789 A1     Sep. 28, 2023

(30) Foreign Application Priority Data

Mar. 23, 2022     (CN) ......................... 202210292949.8

(51) Int. Cl.
| | |
|---|---|
| *B33Y 80/00* | (2015.01) |
| *A61F 2/28* | (2006.01) |
| *A61F 2/30* | (2006.01) |
| *A61L 27/44* | (2006.01) |

(Continued)

(52) U.S. Cl.
CPC ........ *A61F 2/30771* (2013.01); *A61L 27/446* (2013.01); *B33Y 40/20* (2020.01); *B33Y 70/10* (2020.01); *B33Y 80/00* (2014.12); *A61F*
*2002/2835* (2013.01); *A61F 2002/3092* (2013.01); *A61F 2002/30985* (2013.01); *A61L 2430/02* (2013.01)

(58) Field of Classification Search
None
See application file for complete search history.

(56) References Cited

U.S. PATENT DOCUMENTS

2014/0296996 A1 * 10/2014 Shim ....................... A61L 27/32
427/2.27

FOREIGN PATENT DOCUMENTS

| | | | | | |
|---|---|---|---|---|---|
| CN | 109675103 A | * | 4/2019 | ......... | A61L 27/3834 |
| WO | WO-2015173020 A1 | * | 11/2015 | ......... | A61L 27/3821 |

* cited by examiner

*Primary Examiner* — Javier G Blanco
(74) *Attorney, Agent, or Firm* — Hemisphere Law, PLLC

(57)     ABSTRACT

A 3D printed bone defect repair scaffold is provided and prepared by steps of: S1, dissolving a gelatin, sodium alginate and a 58S bioglass in water to obtain a solution, and mass-to-volume concentrations of components in the solution being that the gelatin is 16%, the sodium alginate is 6.5% and the 58S bioglass is 8.5%; S2, stirring the solution to obtain 3D printing slurry, and then conducting 3D printing, the 3D printing being performed with a nozzle with an opening diameter of 0.41 mm at a printing speed of 6 mm/s under a pressure of 0.38 Mpa and a temperature of 29° C.; S3, obtaining a semi-finished scaffold after the 3D printing, performing chemical crosslinking of the semi-finished scaffold with a calcium chloride solution for 8-15 min and then immersing in a glutaraldehyde solution for chemical crosslinking for 1.5-2.5 hours, and finally cleaning and lyophilizing.

8 Claims, 5 Drawing Sheets

(51) Int. Cl.
      *B33Y 40/20*      (2020.01)
      *B33Y 70/10*      (2020.01)

THREE-DIMENSIONAL PRINTED BONE DEFECT REPAIR SCAFFOLD AND PREPARATION METHOD THEREOF

TECHNICAL FIELD

The invention relates to the field of bone tissue engineering repair and reconstruction technologies, and particularly to a three-dimensional (3D) printed bone defect repair scaffold.

BACKGROUND

With the increase of bone tissue damage caused by aging, joint degenerative diseases, and injuries of traffic accidents, bone defect repair has been paid more and more attention. Bone transplantation methods such as autogenous bone transplantation, allogeneic bone transplantation and artificial bone transplantation are usually used in clinical practices. The autogenous bone transplantation is the "gold standard" for defect repair, but the autogenous bone is limited in source and often in short supply. The allogeneic bone transplantation has the risk of infectious diseases, while the artificial bone transplantation lacks osteoinductive activity, has poor osteogenic efficiency, and is difficult to form new tissue with similar structure to healthy bone tissue. Therefore, the research of new regenerative bone defect repair materials with high bioactivity and high efficiency of bone formation has become the difficulty and hot spot in recent years, and has a huge clinical demand and market prospects. In recent years, the new regenerative bone defect repair materials commonly used in clinic are divided into synthetic materials and biomaterials. The synthetic materials have significant advantages in the aspects of strength and configuration, but their compatibility and degradability in vivo need to be improved; while the biomaterials have good compatibility and degradability, but their strengths and shapes are difficult to meet the requirements.

PURPOSE OF INVENTION

The bone defect repair materials usually need to have good mechanical properties, biocompatibility, osteoconductivity and osteoinductivity. Because a scaffold with a three-dimensional structure is more conducive to cell differentiation and proliferation, the bone defect repair materials are generally used in clinic in the form of scaffolds. A bioactive glass is an important scaffold material for bone tissue engineering, which can effectively promote biomineralization in vivo and release silicon and calcium ions to promote osteogenesis and vascularization of stem cells. Gelatin/sodium alginate hydrogel is a mixture of natural polymer materials, which has advantages such as good biocompatibility, tissue absorbability and low immunogenicity, especially it is conducive to combining with high bioactivity inorganic powder for 3D printing, but its mechanical strength is relatively poor. It may be feasible to combine the three materials to prepare a 3D printed scaffold with good strength, biocompatibility and degradability and high osteogenesis efficiency. Some embodiments of the invention intend to use a bioceramic material such as a 58S bioactive glass (58S BG), a polymer material such as a gelatin (Gel), and sodium alginate (SA) as a scaffold base material, study and adjust contents of various components and process parameters of the 3D printing, and prepare a composite biological scaffold for bone defect repair by the 3D printing.

SUMMARY

An objective of the invention is to provide a 3D printed bone defect repair scaffold, which uses a gelatin, sodium alginate and a 58S bioglass as raw materials and adjusts a content ratio of the three raw materials, so that a prepared scaffold has high mechanical strength, good compatibility, good degradability and good bioactivity, and an osteogenesis efficiency of bone tissue is significantly improved.

To achieve the above objective, technical solutions of embodiments of the invention are as follows.

Specifically, a 3D printed bone defect repair scaffold is a multilayer cross-linked porous network structure, in which a first layer includes a plurality of lines mutually parallel, a second layer includes a plurality of lines mutually parallel and perpendicularly connected to an upper surface of the lines of the first layer, and a third layer includes a plurality of lines mutually parallel and perpendicularly connected to an upper surface of the lines of the second layer, and so on. A diameter of each of the plurality of lines of each layer of the 3D printed bone defect repair scaffold is in a range of 300 μm to 500 μm, and a distance between adjacent ones of the plurality of lines of each layer of the 3D printed bone defect repair scaffold is in a range of 500 μm to 700 μm.

Moreover, the 3D printed bone defect repair scaffold is prepared by steps including:

S1, dissolving a gelatin, sodium alginate and a 58S bioglass in water to obtain a solution, wherein mass-to-volume concentrations of components in the solution are that: the gelatin is 16%, the sodium alginate is 6.5%, and the 58S bioglass is 8.5%;

S2, stirring the solution to obtain a 3D printing slurry and then performing 3D printing, wherein the 3D printing was performed with a nozzle with an opening diameter of 0.41 millimeter (mm) at a printing speed of 6 millimeter per second (mm/s) under a pressure of 0.38 megapascals (Mpa) and a temperature of 29 degrees Celsius (° C.); and S3, obtaining a semi-finished scaffold after the 3D printing, performing chemical crosslinking of the semi-finished scaffold with a calcium chloride solution for 8 minutes (min) to 15 min and then immersing in a glutaraldehyde solution for chemical crosslinking for 1.5 hours to 2.5 hours, and subsequently cleaning and lyophilizing.

As a scaffold material for bone repair, it must meet the following conditions that: 1. biodegradation would not produce toxic substances; 2. can provide good mechanical support for new tissue; 3. a rate of degradation matches a rate of tissue regeneration; 4. has pores for allowing dispersion/diffusion of nutrients and metabolites; and 5. can match compressive properties of the scaffold and normal cartilage. In the embodiment of the invention, the sodium alginate gel has a three-dimensional culture structure suitable for cell nutrition exchange, can maintain a specific form formed due to large surface area and many pores, and has good biocompatibility. Addition of the gelatin can improve the mechanical strength of the sodium alginate gel, simulate an internal environment required by cell growth, and achieve good biocompatibility. The 58S bioglass can stably release silicon (Si) ions, calcium (Ca) ions and the like in the scaffold, and can stimulate osteoprogenitor cells at the gene level and promote the growth of new bone.

The selection of contents of the gelatin, the sodium alginate and the 58S bioglass has a great influence on the overall performance of the scaffold. A high content of the gelatin can obtain good biocompatibility, the sodium alginate has a good ability of consolidation forming, and the bioglass promotes the growth of bone. Therefore, how to adjust the contents of the three substances to obtain a scaffold with good biocompatibility, cell adhesion and bio-degradability and high strength requires a lot of experimental work. After a lot of experimental researches, inventors selected mass-to-volume concentrations of components as that the gelatin is 16%, the sodium alginate is 6.5% and the 58S bioglass is 8.5%; and the selection of the concentrations of the above components makes it is easier to mix uniformly and a viscosity is appropriate, so that the 3D printing is smoother, the uniformity is better, a structure of the printed scaffold is more regular, and a porosity and a spacing are more qualified. In addition, an embodiment of the invention properly reduces the printing speed so as to reduce an excessive stretching of output silks in the printing process, which can ensure the structural strength of the scaffold, improve the elastic modulus of the scaffold, provide good mechanical support for new tissue, and match the compressive properties of the scaffold and normal cartilage.

Structural holes of the prepared 3D printed bone defect repair scaffold according to some embodiments are straight, and because of the regular structure, there is no obvious obstacle, and thus no strong fluid resistance exists in fluid mechanics, which is beneficial for nutrients and cells to permeate into the scaffold, and thus the osteogenesis efficiency in the repair process is accelerated.

In an embodiment of the invention, a contour of the 3D printed bone defect repair scaffold is one selected from the group consisting of a cylinder, a cuboid and a cone; and an internal pore structure of the 3D printed bone defect repair scaffold in shape is one selected from the group consisting of a circle, a square, a trapezoid, a triangle and a rhombus. The structure and shape of the scaffold can be conventionally designed as required, and the listed contour and pore structure have good effects on cell adhesion and proliferation.

In an embodiment of the invention, a porosity of the 3D printed bone defect repair scaffold is in a range of 40% to 50%, and an average Young's modulus of the 3D printed bone defect repair scaffold is in a range of 280 kPa to 300 kPa. By adjusting and optimizing contents of the gelatin, the sodium alginate and the 58S bioglass, good elasticity can be achieved and thus can realize good compression resistance when applied to bone tissue repair.

In an embodiment of the invention, the 58S bioglass is ground and then sieved to obtain 58S bioglass powder, and a particle diameter range of the 58S bioglass powder is 4 μm to 10 μm, and a chemical composition of the 58S bioglass is 58% $SiO_2$-33% CaO-9% $P_2O_5$, i.e., is composed of silicon dioxide ($SiO_2$), calcium oxide (CaO) and phosphorous pentoxide ($P_2O_5$) in mass percents of 58%, 33% and 9%, respectively. The selection of particle size (also referred to as grain size) of the 58S bioglass powder makes its specific surface area large, and more ions can be released; and if the particle size is less than 4 μm, its dispersion uniformity in a solution becomes poor, which is not conducive to its effectiveness.

In an embodiment of the invention, in the S3, the semi-finished scaffold is chemically crosslinked with the calcium chloride solution for 10 min and then immersed in the glutaraldehyde solution for chemical crosslinking for 2 hours, and subsequently cleaned and lyophilized. The selection of crosslinking times in the embodiment of the invention makes the degree of crosslinking appropriate, which not only enhances the mechanical property of the scaffold, but also prevents the scaffold from becoming brittle due to excessive crosslinking density.

In an embodiment of the invention, the calcium chloride solution has a concentration in a range of 5% to 6%, and is prepared by dissolving calcium chloride powder in distilled water. Strengths of sodium alginate and gelatin are obtained by using the crosslinking and a polyelectrolyte effect therebetween. The sodium alginate can be complexed with $Ca^{2+}$ to form a hydrogel, and a main reaction mechanism is that a G unit (b-D guluronic acid) are complexed and crosslinked with $Ca^{2+}$ to form an egg-box structure, and G groups are stacked to form a crosslinked network structure and transform into the hydrogel. The concentration setting of the calcium chloride solution makes a gelation speed of the sodium alginate appropriate.

In an embodiment of the invention, the glutaraldehyde solution has a concentration in a range of 1.0% to 1.5%, and is prepared by diluting a glutaraldehyde solution with a concentration of 50% with distilled water. The glutaraldehyde reacts with the gelatin, which can further improve the structural strength of the scaffold. The embodiment of the invention adjusts the concentration of the glutaraldehyde solution and controls the degree of crosslinking reaction, which makes the scaffold have good mechanical property and be not easy to embrittle.

In some embodiments of the invention, in the S2, the 3D printing slurry is injected into a 3D printing material barrel, defoamed and homogenized, and then printing is started. In the S2, the solution is stirred to be uniform through magnetic stirring and/or mechanical stirring to obtain the 3D printing slurry. After being stirred to be uniform, the printing slurry is defoamed and homogenized, and then 3D printing is carried out, so that uniformity of the printing slurry is better.

Moreover, an embodiment of the invention further provides an application of the 3D printing bone defect repair scaffold in promoting formation of bone tissue and vascular tissue. For example, the 3D printing bone defect repair scaffold is implanted into a bone defect area to promote formation of bone tissue and vascular tissue.

Compared with the prior art, the various embodiments of the invention may achieve beneficial effects as follows.

1. The embodiments of the invention, based on a lot of experimental researches, select mass-to-volume concentrations of components as that the gelatin is 16%, the sodium alginate is 6.5% and the 58S bioglass is 8.5%. The selection of the concentrations of the above components makes it is easier to mix uniformly and a viscosity is appropriate, so that the 3D printing is smoother, the uniformity is better, a structure of the printed scaffold is more regular, and a porosity and a spacing are more qualified.

2. Some embodiments of the invention properly reduce the printing speed so as to reduce an excessive stretching of output silks in the printing process, which can ensure the structural strength of the scaffold, improve the elastic modulus of the scaffold, improve the swelling property of the scaffold, and promotes cell proliferation and adhesion. Structural holes of the prepared 3D printed bone defect repair scaffold are straight, and because of the regular structure, there is no obvious obstacle, and thus no strong fluid resistance exists in fluid mechanics, which is beneficial for nutrients and cells to permeate into the scaffold, and thus the osteogenesis efficiency in the repair process is accelerated.

3. A porosity of the 3D printed bone defect repair scaffold is in a range of 40% to 50%, and an average Young's modulus of the 3D printed bone defect repair scaffold is in a range of 280 kPa to 300 kPa.

DETAILED DESCRIPTION OF EMBODIMENTS

Figure 1A:
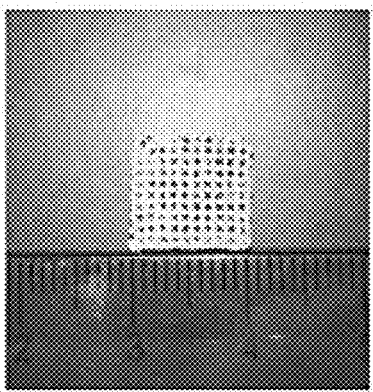
FIG. 1A and FIG. 1B respectively are a front viewed photo and a side viewed photo of a 3D printed scaffold according to an embodiment of the invention.

In order to make purposes, technical solutions and advantages of embodiments of the invention more clear, the invention is further described in detail below in conjunction with the accompanying drawings and illustrated embodiments, but the scope of protection of the invention is not limited to the illustrated embodiments.

Raw materials used in the following illustrated embodiments are commercially available, unless otherwise specified.

A 58S bioglass as used has a chemical composition of 58% $SiO_2$-33% CaO-9% $P_2O_5$, and a diameter range of 4 to 10 microns (μm) in powder form.

Embodiment 1

A 3D printed bone defect repair scaffold is a multilayer cross-linked porous network structure. In particular, for the multilayer cross-linked porous network structure, a first layer includes multiple (i.e., more than one) mutually parallel lines, a second layer includes multiple mutually parallel lines perpendicular to an upper surface of the multiple lines of the first layer, a third layer includes multiple mutually parallel lines perpendicular to an upper surface of the multiple lines of the second layer, and so on. In each the layer of the 3D printed bone defect repair scaffold, a diameter of each of the multiple lines is about 500 μm, and a distance between adjacent ones of the multiple lines is about 700 μm.

A preparation method of the 3D printed bone defect repair scaffold includes the following steps S1 to S3.

S1, dissolving gelatin, sodium alginate and 58S bioglass in water to obtain a solution. Mass-to-volume (m/v) concentrations of components in the solution are that: the gelatin is 16%, sodium alginate is 6.5%, and the 58S bioglass is 8.5%.

S2, stirring the solution to be uniform to obtain a 3D printing slurry, and then performing 3D printing. The 3D printing was performed with a nozzle with an opening diameter of 0.41 millimeters (mm) at a printing speed of 6 millimeter per second (mm/s) under a pressure of 0.38 megapascals (Mpa) and a temperature of 29 degrees Celsius (° C.).

S3, obtaining a semi-finished scaffold after the 3D printing, performing chemical crosslinking of the semi-finished scaffold with a calcium chloride solution for 8 minutes (min) and then immersing in a glutaraldehyde solution for chemical crosslinking for 2.5 hours, and subsequently cleaning and lyophilizing, to prepare the 3D printed bone defect repair scaffold consequently.

Embodiment 2

A 3D printed bone defect repair scaffold is a multilayer cross-linked porous network structure. In particular, for the multilayer cross-linked porous network structure, a first layer includes multiple mutually parallel lines, a second layer includes multiple mutually parallel lines perpendicular to an upper surface of the multiple lines of the first layer, a third layer includes multiple mutually parallel lines perpendicular to an upper surface of the multiple lines of the second layer, and so on. In each the layer of the 3D printed bone defect repair scaffold, a diameter of each of the multiple lines is about 400 μm, and a distance between adjacent ones of the multiple lines is about 600 sm.

A preparation method of the 3D printed bone defect repair scaffold includes the following steps S1 to S3.

S1, dissolving gelatin, sodium alginate and 58S bioglass in water to obtain a solution. Mass-to-volume (m/v) concentrations of components in the solution are that: the gelatin is 16%, sodium alginate is 6.5%, and the 58S bioglass is 8.5%.

S2, stirring the solution to be even to obtain a 3D printing slurry, and then performing 3D printing. The 3D printing was performed with a nozzle with an opening diameter of 0.41 mm at a printing speed of 6 mm/s under a pressure of 0.38 Mpa and a temperature of 29° C.

S3, obtaining a semi-finished scaffold after the 3D printing, performing chemical crosslinking of the semi-finished scaffold with a calcium chloride solution for 10 min and then immersing in a glutaraldehyde solution for chemical crosslinking for 2.0 hours, and subsequently cleaning and lyophilizing, to prepare the 3D printed bone defect repair scaffold consequently.

Embodiment 3

A 3D printed bone defect repair scaffold is a multilayer cross-linked porous network structure. In particular, for the multilayer cross-linked porous network structure, a first layer includes multiple mutually parallel lines, a second layer includes multiple mutually parallel lines perpendicular to an upper surface of the lines of the first layer, a third layer includes multiple mutually parallel lines perpendicular to an upper surface of the lines of the second layer, and so on. In each the layer of the 3D printed bone defect repair scaffold, a diameter of each of the multiple lines is about 400 μm, and a distance between adjacent ones of the multiple lines is about 500 μm.

A preparation method of the 3D printed bone defect repair scaffold includes the following steps S1 to S3.

S1, dissolving gelatin, sodium alginate and 58S bioglass in water to obtain a solution. Mass-to-volume (m/v) concentrations of components in the solution are that: the gelatin is 16%, sodium alginate is 6.5%, and the 58S bioglass is 8.5%.

S2, stirring the solution to be even to obtain a 3D printing slurry, and then performing 3D printing. The 3D printing was performed with a nozzle with an opening diameter of 0.41 mm at a printing speed of 6 mm/s under a pressure of 0.38 Mpa and a temperature of 29° C.

S3, obtaining a semi-finished scaffold after the 3D printing, performing chemical crosslinking of the semi-finished scaffold with a calcium chloride solution for 15 min and then immersing in a glutaraldehyde solution for chemical crosslinking for 1.5 hours, and subsequently cleaning and lyophilizing, to prepare the 3D printed bone defect repair scaffold consequently.

Performance Testing

The 3D printed bone defect repair scaffold prepared by the above embodiment 2 as an example was performed with a performance testing as follows.

Figure 1B:
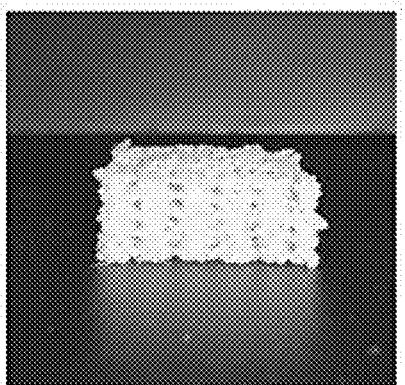

1. Photographing, photos for displaying structural sizes of the 3D printed bone defect repair scaffold are shown in FIGS. 1A and 1B.

2. Degradability test: the 3D printed bone defect repair scaffold was immersed in simulated body fluid, then taken out every 7 days and weighed after absorbing water with a filter paper, and afterwards put into new simulated body fluid. Finally, a degradation weight change curve of the 3D printed bone defect repair scaffold was drawn.

3. Mechanical property test: the 3D printed bone defect repair scaffold was immersed in a phosphate buffer saline (PBS), then taken out after 24 hours and water was absorbed by a filter paper, and afterwards the scaffold was placed on a universal mechanical tester and loaded with 10 kilonewtons (kN) pressure. Finally, a stress-displacement curve was drawn.

4. Elasticity test: the 3D printed bone defect repair scaffolds each with a width of 10 mm were compressed and placed into mold channels with respective widths of 7 mm, 6 mm and 5 mm, and after passing through the respective mold channels, deformation recovery and structural integrity of each of the scaffolds was observed.

5. Polymerase Chain Reaction (PCR) test: rBMSCs were seeded on the 3D-printed bone defect repair scaffold as per 10s per hole (10 s/hole), cultured in low-glucose Dulbecco's modified eagle medium (DMEM) containing 10% fetal bovine serum (FBS), performed with fluid replacement one time every 3 days, extracted with total ribonucleic acids (RNAs) of cells on the 7th, 14th and 21st days and performed with PCR test.

6. Animal experiment

Sixty-four specific pathogen-free (SPF) male Sprague-Dawley (SD) rats, each with a weight of 280-320 grams, were randomly divided into a scaffold group and a control group (blank control). Each of the rats was anesthetized by intraperitoneal injection under aseptic condition, and a 1.0-1.5 cm incision was made on a lower edge parallel to its mandible. The mandible was exposed by blunt dissection after subcutaneous tissue was incised in layers, a circular full-thickness bone defect with a diameter of 5 mm was made by using a bone trephine drill with a diameter of 5 mm and physiological saline (also referred to as normal saline) perfusion and cooling. In the scaffold group, the scaffold was implanted into a critical-sized bone defect in the mandible of each rat; while in the control group, no scaffold was implanted, which was only used as a blank control. Sampling was performed at 4 weeks (4 w) and 8 weeks (8 w) after implantation, bone formations were detected by microCT and HE staining, intra-tissue wounds were sutured in layers with 5-0 sutures, and penicillin sodium was injected intramuscularly for 3 consecutive days after operation to resist infection. Samples were obtained at two time points of 4 weeks and 8 weeks, the rats were euthanized by carbon dioxide asphyxiation, and the mandible containing the defect area of each the rat was removed and fixed in 10% neutral buffered formalin for 24 hours, and then microCT scanning was performed. Image files were scanned and reconstructed using the NRecon software Skyscan, and regions of interest (ROIs) were selected from the scanned images, for analysis.

As seen from FIGS. 1A and 1B, structural holes of the prepared 3D printed bone defect repair scaffold are straight, and because of the regular structure, there is no obvious obstacle, and thus no strong fluid resistance exists in fluid mechanics, which is beneficial for nutrients and cells to permeate into the scaffold, and thus the osteogenesis efficiency in the repair process is accelerated. After being tested, a porosity of the scaffold is 45%.

Figure 2:
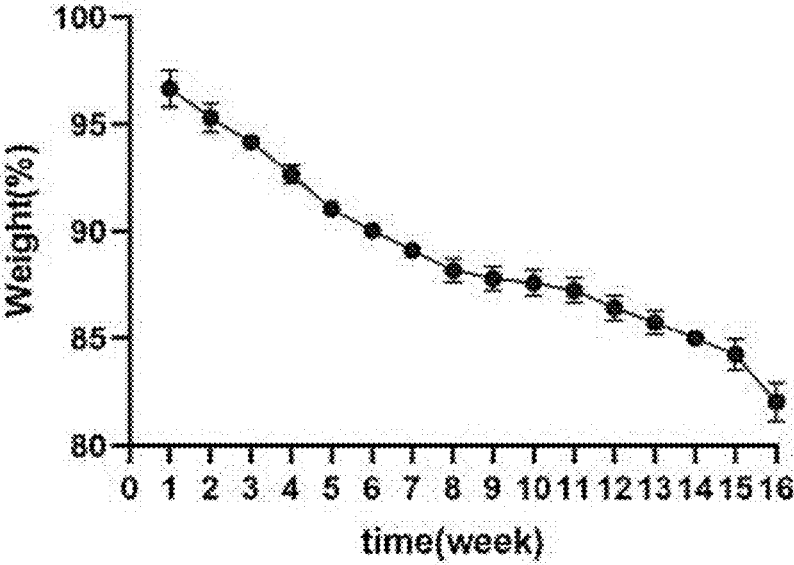
FIG. 2 illustrates a schematic weight change curve during degradation of the 3D printed scaffold according to an embodiment of the invention.
Figure 3:
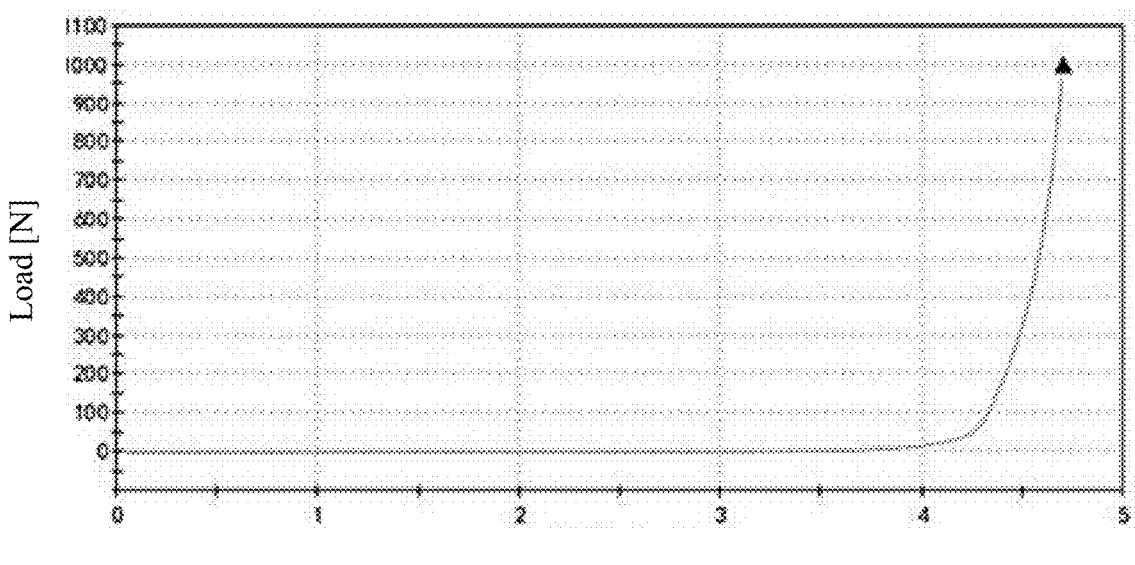
FIG. 3 illustrates a schematic a stress-displacement curve during degradation of the 3D printed scaffold according to an embodiment of the invention.
Figure 4:
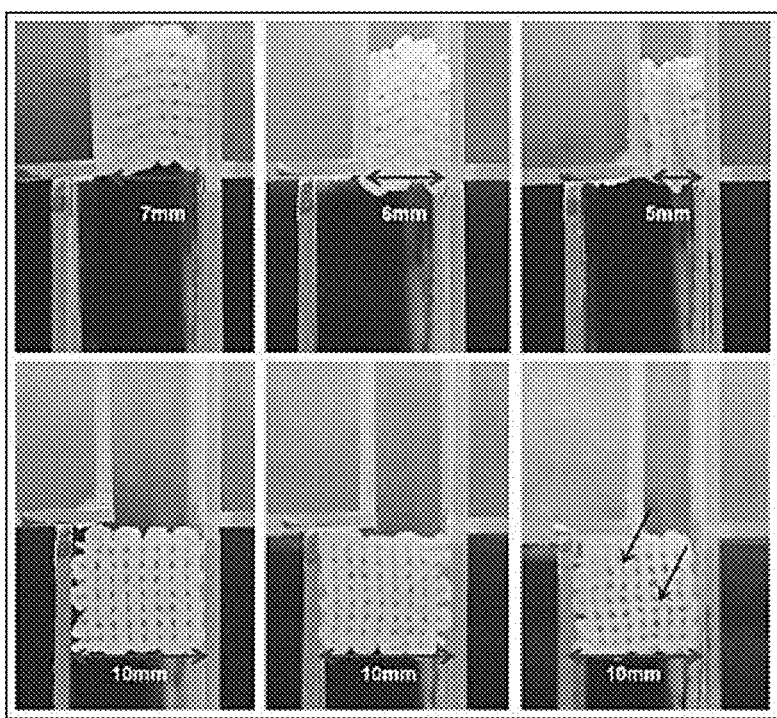
FIG. 4 illustrates a schematic diagram of recovery after compression of the 3D printed scaffold according to an embodiment of the invention.

As seen from FIG. 2 and FIG. 3, it can be found that the 3D printed bone defect repair scaffold has good degradability and mechanical property, and an average Young's modulus of the scaffold is 290 kPa after estimation. As seen from FIG. 4, it can be found that the 3D printed bone defect repair scaffold has good elasticity.

Figure 5:
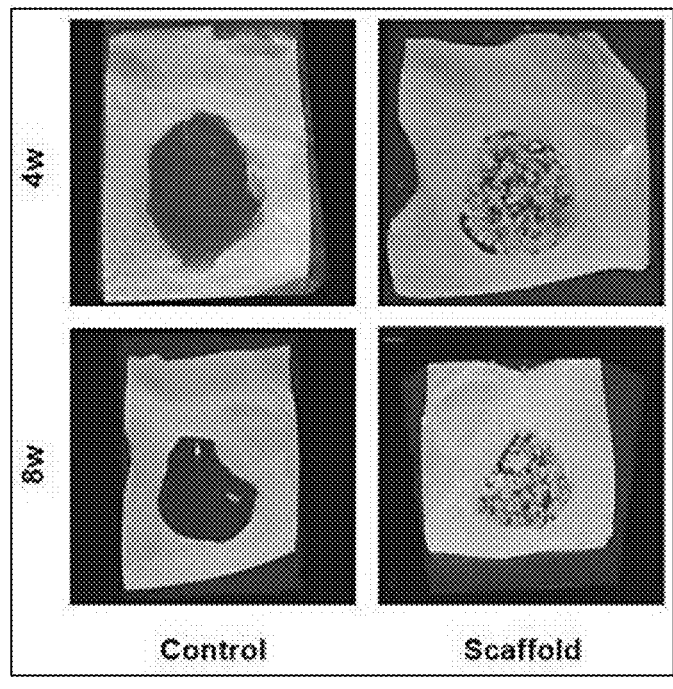
FIG. 5 illustrates microCT (abbreviation of "micro computed tomography") images of bone defect repairs of a rat jawbone defect model after being implanted with the 3D printed scaffold according to an embodiment of the invention.
Figure 6:
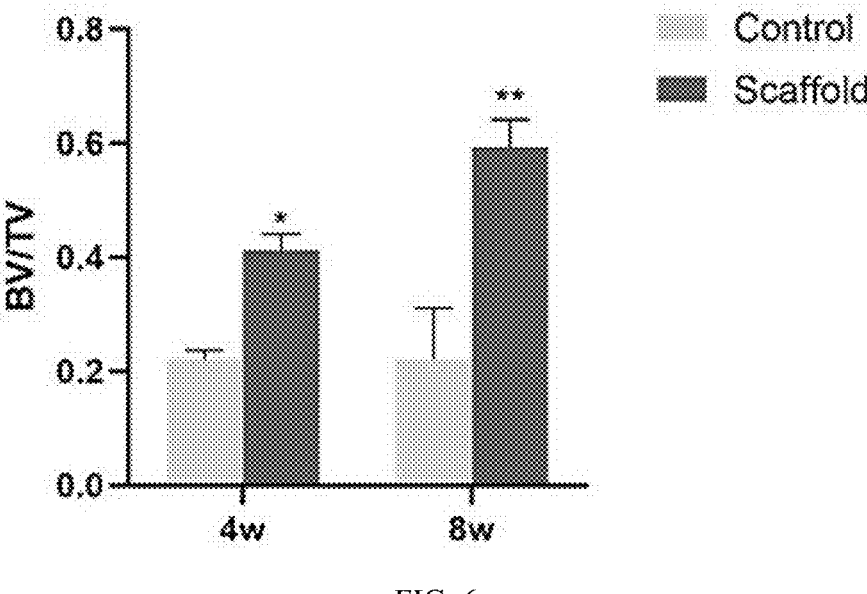
FIG. 6 illustrates a schematic diagram of bone volume quantitative analysis on bone defect repairs of a rat jawbone defect model after being implanted with the 3D printed scaffold according to an embodiment of the invention.
Figure 7:
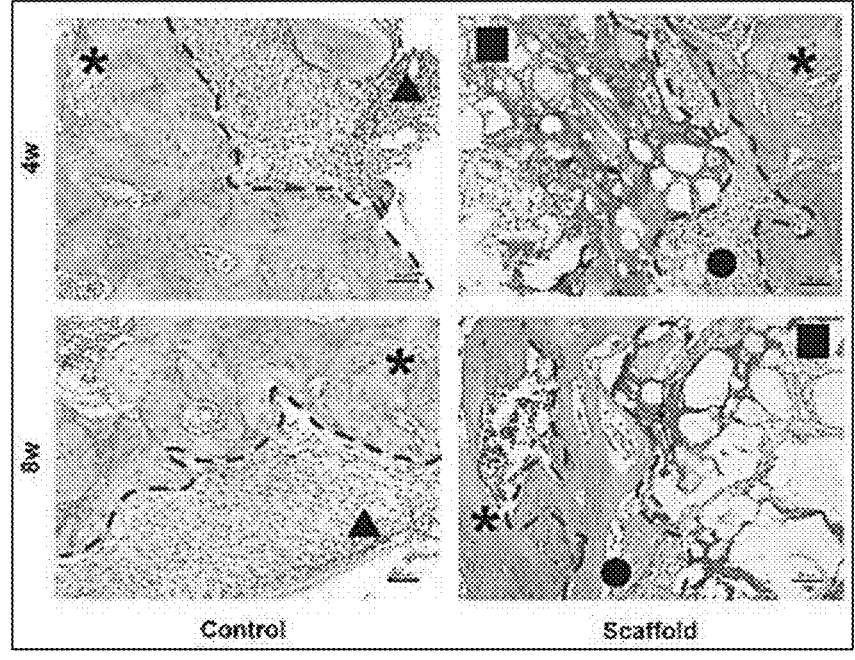
FIG. 7 illustrates a schematic diagram of hematoxylin-eosin (HE) staining on bone defect repairs of a rat jawbone defect model after being implanted with the 3D printed scaffold according to an embodiment of the invention; in which, the sign of asterisk denotes normal bone tissue at an edge of a defect area, the sign of triangle denotes fibrous tissue, the sign of circle denotes neogenetic bone tissue, and the sign of rectangle denotes the scaffold.
Figure 8:
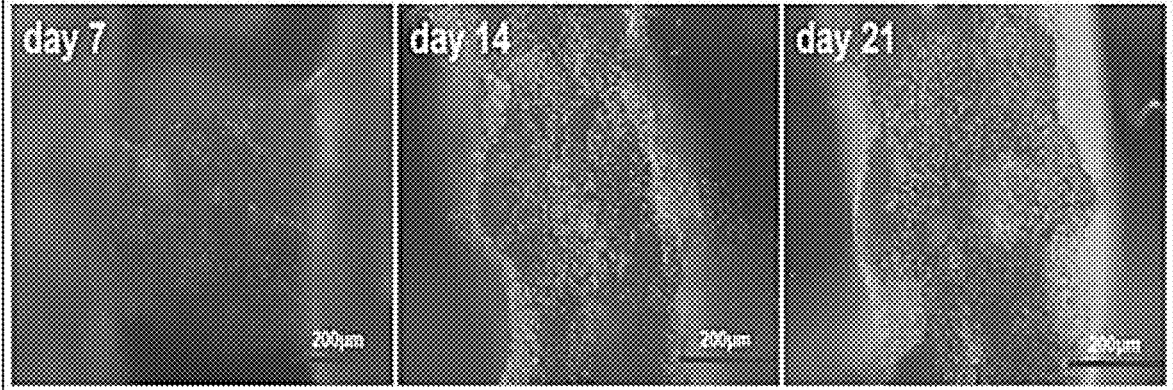
FIG. 8 illustrates a schematic diagram of 4',6-diamidino-2-phenylindole (DAPA) straining for displaying rat bone marrow mesenchymal stem cells (rBMSCs) adhered and proliferated on a surface of the scaffold according to an embodiment of the invention.
Figures 9A, 9B, 9C:
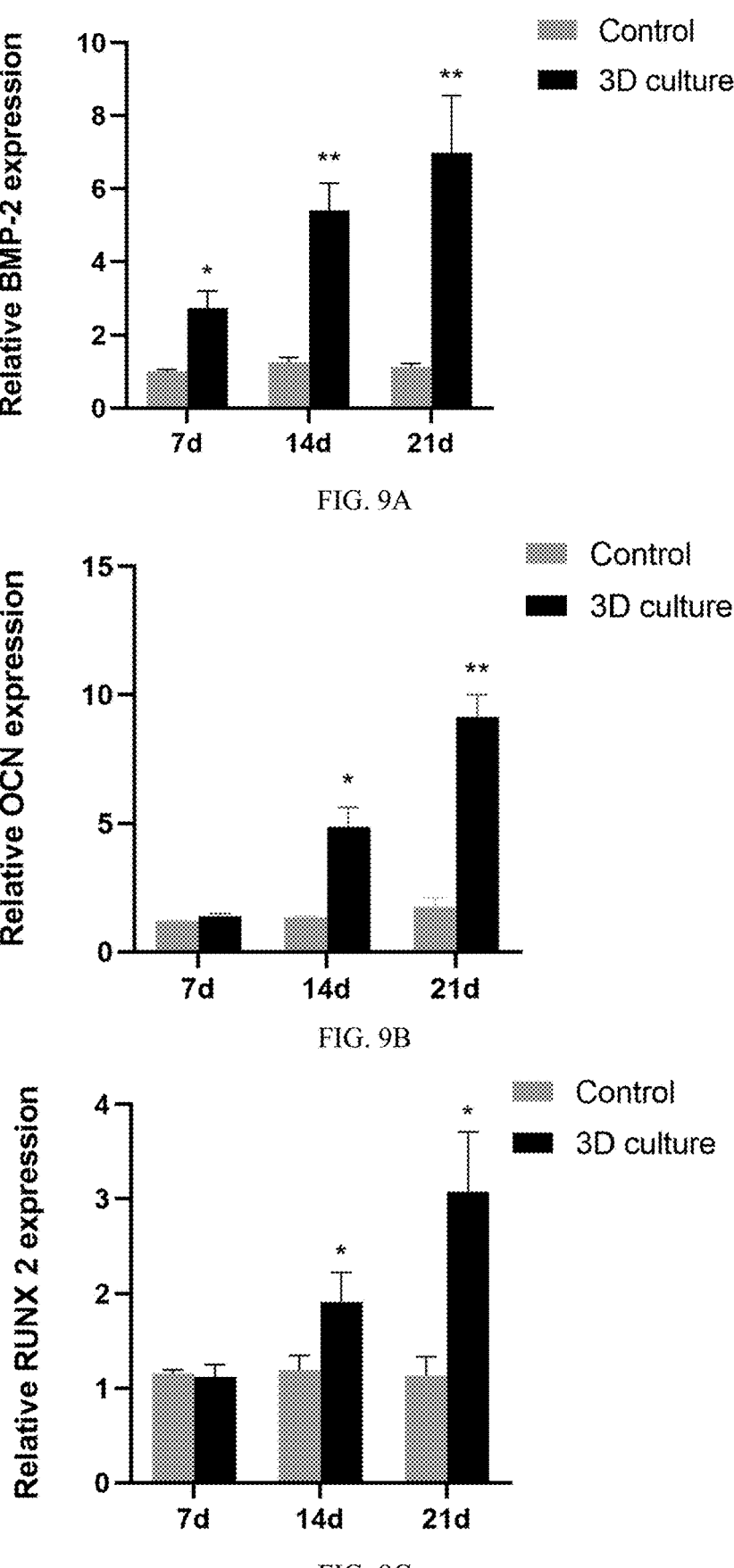
FIGS. 9A-9C respectively illustrate expression levels of bone formation-related genes of bone morphogenetic protein 2 (BMP-2), osteocalcin (OCN) and runt-related transcription factor 2 (RUNX2).

As seen from FIG. 5, FIG. 6 and FIG. 7, it can be found that the prepared 3D printed bone defect repair scaffold has good osteogenic effect.

rBMSCs were colonized on the 3D printed bone defect repair scaffold and cultured for 7, 14, 21 days, DAPA staining results showed that the rBMSC can adhere and proliferate on the scaffold (see FIG. 8). After the rBMSCs were seeded on the 3D-printed bone defect repair scaffold, total RNAs were extracted and a PCR test was performed, and results showed that expression levels of rBMSC osteogenesis-related genes BMP-2, OCN and RUNX2 cultured on the scaffold were increased (see FIGS. 9A-9C).

As seen from the above test results, the 3D printed bone defect repair scaffold prepared by illustrated embodiment of the invention achieves the objective of the invention, has good degradability, an average Young's modulus of 290 kPa, good elasticity, can effectively promote the formation of bone tissue and vascular tissue, and has good osteogenesis effect.

According to the disclosure and teachings of the foregoing description, those skilled in the art can make changes and modifications to the above-described embodiments. Therefore, the invention is not limited to the embodiments disclosed and described above, and certain modifications and changes to the embodiments of the invention are intended to fall within the scope of the appended claims. In addition, although specific terms are used in the above description, these terms are only for convenience of illustration and do not constitute any limitation to the invention.

What is claimed is:

1. A preparation method of a 3D printed bone defect repair scaffold, comprising:

step 1, dissolving a gelatin, sodium alginate, and a 58S bioglass in water to obtain a solution, wherein mass-to-volume concentrations of components in the solution are that: the gelatin is 16%, the sodium alginate is 6.5%, and the 58S bioglass is 8.5%; the 58S bioglass is in powder form and composed of silicon dioxide ($SiO_2$), calcium oxide (CaO) and phosphorous pentoxide ($P_2O_5$) in mass percents of 58%, 33% and 9%, respectively;

step 2, stirring the solution to obtain 3D printing slurry and then performing 3D printing, wherein the 3D printing was performed with a nozzle with an opening diameter of 0.41 millimeter (mm) at a printing speed of 6 millimeter per second (mm/s) under a pressure of 0.38 megapascals (Mpa) and a temperature of 29 degrees Celsius (C); and step 3, obtaining a semi-finished scaffold after the 3D printing, performing chemical crosslinking of the semi-finished scaffold with a calcium chloride solution for 8 minutes (min) to 15 minutes and then immersing in a glutaraldehyde solution for chemical crosslinking for 1.5 hours to 2.5 hours, and subsequently cleaning and lyophilizing, to thereby obtain the 3D printed bone defect repair scaffold;

wherein the 3D printed bone defect repair scaffold is a multilayer cross-linked porous network structure, in which a first layer comprises a plurality of lines mutually parallel, a second layer comprises a plurality of lines mutually parallel and perpendicularly connected to an upper surface of the lines of the first layer, and a third layer comprises a plurality of lines mutually parallel and perpendicularly connected to an upper surface of the lines of the second layer; a diameter of each of the plurality of lines of each layer of the 3D printed bone defect repair scaffold is in a range of 300 micrometers ($\mu m$) to 500 $\mu m$, and a distance between adjacent ones of the plurality of lines of each layer of the 3D printed bone defect repair scaffold is in a range of 500 $\mu m$ to 700 $\mu m$, wherein a contour of the 3D printed bone defect repair scaffold is one selected from the group consisting of a cylinder, a cuboid, and a cone; and an internal pore structure of the 3D printed bone defect repair scaffold in shape is one selected from the group consisting of a circle, a square, a trapezoid, a triangle, and a rhombus, wherein the 3D printed bone defect repair scaffold is sized and configured to promote formation of bone tissue.

2. The preparation method of a 3D printed bone defect repair scaffold according to claim 1, wherein a porosity of the 3D printed bone defect repair scaffold is in a range of 40% to 50%, and an average Young's modulus of the 3D printed bone defect repair scaffold is in a range of 280 kilopascals (kPa) to 300 kPa.

3. The preparation method of a 3D printed bone defect repair scaffold according to claim 1, wherein the 58S bioglass is ground and then sieved to obtain 58S bioglass powder, and a particle diameter range of the 58S bioglass powder is 4 $\mu m$ to 10 $\mu m$.

4. The preparation method of a 3D printed bone defect repair scaffold according to claim 1, wherein in the S3, the semi-finished scaffold is chemically crosslinked with the calcium chloride solution for 10 min and then immersed in the glutaraldehyde solution for chemical crosslinking for 2 hours, and subsequently cleaned and lyophilized.

5. The preparation method of a 3D printed bone defect repair scaffold according to claim 1, wherein the calcium chloride solution has a concentration in a range of 5% to 6%, and is prepared by dissolving calcium chloride powder in distilled water.

6. The preparation method of a 3D printed bone defect repair scaffold according to claim 1, wherein the glutaraldehyde solution has a concentration in a range of 1.0% to 1.5%, and is prepared by diluting a glutaraldehyde solution with a concentration of 50% through distilled water.

7. The preparation method of a 3D printed bone defect repair scaffold according to claim 1, wherein in the S2, the 3D printing slurry is injected into a 3D printing material barrel, defoamed and homogenized, and then printing is started.

8. The preparation method of a 3D printed bone defect repair scaffold according to claim 1, wherein in the S2, the solution is stirred through at least one of magnetic stirring and mechanical stirring to obtain the 3D printing slurry.

* * * * *